US005739344A

United States Patent [19]
Pews

[11] Patent Number: 5,739,344
[45] Date of Patent: Apr. 14, 1998

[54] PREPARATION OF AN AMINOARYLAMINOARAZOLE

[75] Inventor: R. Garth Pews, Midland, Mich.

[73] Assignee: The Dow Chemical Company, Midland, Mich.

[21] Appl. No.: 761,406

[22] Filed: Dec. 6, 1996

[51] Int. Cl.$^6$ ............... C07D 235/18; C07D 277/66
[52] U.S. Cl. ............... 548/178; 548/224; 548/310.7; 564/134; 564/139; 564/142
[58] Field of Search ............... 548/224, 178, 548/310.7; 564/134, 139, 142

[56] References Cited

U.S. PATENT DOCUMENTS

| | | | |
|---|---|---|---|
| 4,087,409 | 5/1978 | Preston | 260/65 |
| 4,831,193 | 5/1989 | Lamendola et al. | 564/417 |
| 4,880,926 | 11/1989 | Fujiwara et al. | 544/105 |
| 5,017,280 | 5/1991 | Paris-Marcano | 208/223 |
| 5,223,617 | 6/1993 | Hammond et al. | 544/190 |
| 5,567,843 | 10/1996 | Lysenko | 562/804 |

OTHER PUBLICATIONS

Abdelhamid et al., J. Heterocyclic Chem., vol. 25, pp. 403–405 (1988).

Dondoni et al., Synthesis, pp. 998–1001 (Nov. 1987).

Preston et al., J. Hetertocyclic Chem., vol. 79, pp. 119–120 (1969).

Tsuge et al., Bull. Chem. Soc. Jpn., vol. 60, pp. 2463–2473 (1987).

Tsuge et al., Chemistry Letters, pp. 183–186 (1986).

"Polyamic Acids and Methods to Convert Polyamic Acids into Polyimidebenzoxazole Films" filed in the United States of America on Oct. 31, 1994; Application Serial No. 08/331, 775; Applicants: Wen–Fang Hwang, et al.

*Primary Examiner*—Johann Richter
*Assistant Examiner*—Laura Cross Lutz
*Attorney, Agent, or Firm*—Reid S. Willis

[57] ABSTRACT

An aminoarylaminoarazole can be prepared by a process comprising the steps of condensing a condensable nitroarylcarbonyl compound with an aminonitroarylol, an aminonitroarylthiol, or a triaminonitroarene to form a dinitroanilide, then reducing and cyclizing the dinitroanilide under such conditions to form the aminoarylaminoarazole. The aminoarylaminoarazole is useful in making PIBX polymers.

18 Claims, No Drawings

PREPARATION OF AN AMINOARYLAMINOARAZOLE

BACKGROUND OF THE INVENTION

The present invention relates to the preparation of an aminoarylaminoarazole, particularly an aminoarylaminoaroxazole, an aminoarylaminoarathiazole, or an aminoarylaminoarimidazole.

PIBX (polyimide benzoxazole, polyimide benzothiazole, or polyimide benzimidazole) polymers are useful in the preparation of high performance films that find applications in the electronics industry. These polymers can be prepared by reacting a dianhydride with an aminophenylaminobenzazole, which can be an aminophenylaminobenzoxazole, an aminophenylbenzothiazole, or a aminophenylaminobenzimidazole. See, for example, U.S. Pat. No. 4,087,409, incorporated herein by reference.

An aminophenylaminobenzazole is represented by the following structure:

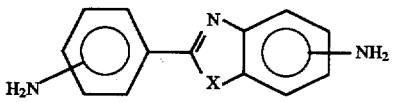

where X is O, S, or NH.

Aminophenylaminobenzazoles can be prepared by reacting an aminobenzoic acid with 2,4- or 2,5-diaminophenol (when X is O), 2,4- or 2,5-diaminophenyl mercaptan (when X is S), or 1,2,4-triaminobenzene (when X is NH) using polyphosphoric acid (PPA) as a solvent. (See Preston et al. in *J. Het. Chem.*, Vol. 79, p. 119 (1969)). Unfortunately, the large quantity of PPA used in this process requires that extensive neutralization be carried out, resulting in the formation of large volumes of aqueous phosphate salts as a waste stream. Also, the product must be purified extensively to be useful as a monomer. Furthermore, the diaminophenol and aminobenzoic acid starting materials are expensive and not readily available.

In U.S. Pat. No. 5,567,843, the diaminobenzazoles are described as being prepared by first contacting an aromatic aldehyde with hydroxylamine to form an aldoxime, then contacting the aromatic aldehyde with a hypohalous acid to from a hydroxamoyl halide, and finally, contacting the hydroxamoyl halide with an aromatic primary amine that has an XH group ortho to the primary amine group, where X is O, S, or NH.

It would be desirable to prepare aminoarylarazoles by a procedure that reduces or eliminates the use of PPA, thereby reducing the formation of costly waste streams. It would further be desirable to improve the overall yield of the desired product.

SUMMARY OF THE INVENTION

In one aspect, the present invention is a process of preparing an aminoarylaminoarazole having the formula:

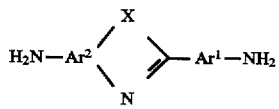

comprising the steps of: a) condensing a condensable nitroarylcarbonyl compound with an aminonitroarylex to form an anilide having the formula:

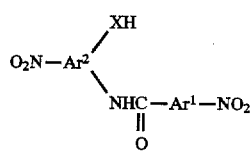

wherein $Ar^1$ and $Ar^2$ are each aromatic groups; X is S, NH, or O; and the —XH and —NHC(O)$Ar^1NO_2$ groups are connected to adjacent carbon atoms on $Ar^2$; and b) cyclizing and reducing the anilide under such conditions to form the aminoarylaminoarazole.

In a second aspect, the present invention is a process of preparing an aminophenylaminobenzazole represented by the following formula:

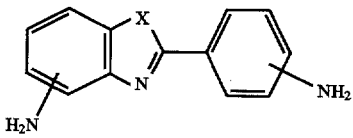

where X is S, NH, or O, comprising the steps of: a) condensing a condensable nitrophenylcarbonyl compound with an aminonitrophenol, a diaminonitrobenzene, or an aminonitrobenzenethiol in the presence of a solvent selected from the group consisting of dioxane, ethylene glycol diethyl ether, diethylene glycol diethyl ether, diethylene glycol dimethyl ether, triethylene glycol dimethyl ether, and tetraethylene glycol dimethyl ether, and at a temperature of from about 100° C. to about 280° C., to form a dinitrobenzanilide having the formula:

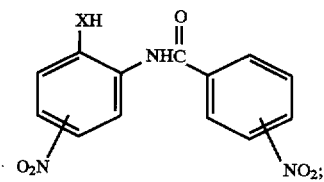

b) adding sufficient heat and a sufficient amount of polyphosphoric acid to a solution containing the solvent and the dinitrobenzanilide to promote the formation of a nitrophenylnitrobenzazole represented by the formula:

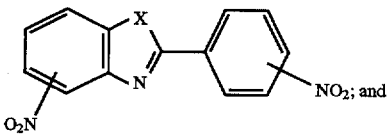

c) reducing the nitrophenylnitrobenzazole with hydrogen and a metal catalyst under such conditions to form the aminophenylaminobenzazole.

In a third aspect, the present invention is a process of preparing an aminoarylaminoarazole having the formula:

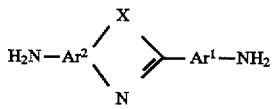

comprising the step of condensing a condensable nitroarylcarbonyl compound with an aminonitroarylex in the presence of a solvent selected from the group consisting of dioxane, ethylene glycol diethyl ether, diethylene glycol diethyl ether, diethylene glycol dimethyl ether, triethylene glycol dimethyl ether, and tetraethylene glycol dimethyl ether, and at a temperature of from about 100° C. to about 280° C., to form an anilide having the formula:

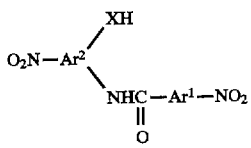

wherein $Ar^1$ and $Ar^2$ are each aromatic groups; X is S, NH, or O; and the —XH and —NHC(O)$Ar^1NO_2$ groups are connected to adjacent carbon atoms on $Ar^2$.

The reducing and cyclizing steps can be performed in any order to achieve the desired final product. The aminoarylaminoarazole can be used to make PIBX.

The process of the present invention provides a way of obtaining the desired product in high yield while reducing costly phosphate waste stream generation.

DETAILED DESCRIPTION OF THE INVENTION

The aminoarylaminoarazole prepared by the process of the present invention is represented by the formula:

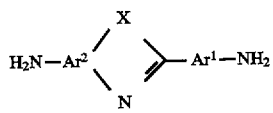

where $Ar^1$ and $Ar^2$ are each aromatic groups. For the purposes of this invention, the aminoarylaminoarazole can be described as an aminoarazole group linked to an aminoaryl group. The term "aminoarazole" is used herein to refer to an aromatic amino [1,3]oxazole, an aromatic amino [1,3]imidazole, or aromatic amino [1,3]thiazole represented by the following fragment:

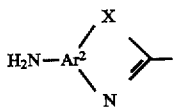

wherein X is S, NH, or O; $Ar^2$ is an aromatic moiety that is fused to the X and the N groups at adjacent carbon atoms on $Ar^2$; and the $NH_2$ group is attached to an aromatic carbon atom on $Ar^2$. $Ar^2$ may also contain non-aromatic groups, such as alkyl groups, which are non-reactive to the condensation, cyclization, and reduction reaction conditions. Examples of aminoarazoles groups include aminobenzoxazoles, aminobenzothiazoles, aminobenzimidazoles, aminonaphthoxazoles, aminonaphthothiazoles, aminonaphthimidazoles, aminoanthroxazoles, aminoanthrothiazoles, aminoanthroimidazoles, aminophenanthroxazoles, aminophenanthrothiazoles, aminophenanthroimidazoles, oxazoloaminopyridines, imidazoleaminopyridines, and thiazolaminopyridines. More preferred aminoarazoles are aminobenzoxazoles and aminobenzothiazoles, with aminobenzoxazoles being most preferred.

The aminoaryl portion of the aminoarylaminoarazole is represented by the fragment:

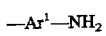

where $Ar^1$ is an aromatic nucleus. Examples of aminoaryl groups include aminophenyl, aminonaphthyl, aminoanthryl, aminophenanthryl, and aminopyridinyl, with aminophenyl being preferred. The preferred aminoarylaminoarazole is represented by the following formula:

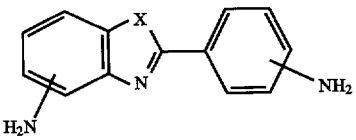

More preferably, X is O. The most preferred aminoarylaminoarazole is represented by the following formula:

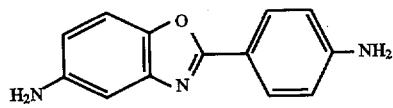

The aminoarylaminoarazoles of the present invention are prepared by first condensing a condensable nitroarylcarbonyl compound (II) with an aminonitroarylex (I) to form a dinitroanilide (III) as illustrated:

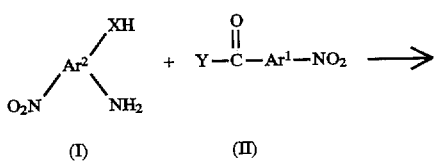

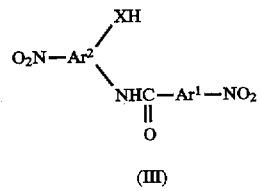

(III)

where Y is OH, OR, Cl, Br, or F; where R is alkyl, aryl, or arylalkyl; and the XH and $NH_2$ groups are attached to adjacent carbon atoms on $Ar^2$. Preferably, Y is Cl, Br, $OC_{1-4}$alkyl, or O-phenyl. More preferably, Y is Cl, Br, or O-phenyl. Most preferably, Y is Cl.

The term "condensable nitroarylcarbonyl compound" is used herein to refer to a nitroaryl carboxylate, a nitroaryl carboxylic acid, or nitroaryl carbonyl halide, as depicted in compound (II). Preferably, the nitroarylcarbonyl compound (II) is a nitrobenzoyl halide, a nitrobenzoic acid, or a $C_{1-4}$ nitrobenzoate, more preferably 4-nitrobenzoyl chloride, 3-nitrobenzoyl chloride, 4-nitrobenzoyl bromide, 3-nitrobenzoyl bromide, methyl 4-nitrobenzoate, methyl 3-nitrobenzoate, phenyl 4-nitrobenzoate, or phenyl 3-nitrobenzoate. The most preferred condensable nitroarylcarbonyl compound (II) is 4-nitrobenzoyl chloride.

The term "aminonitroarylex" is used herein to refer to an aminonitroarylol, a diaminonitroarene, or an aminonitroarylthiol as depicted in structure (I). The preferred aminonitroarylex (I) is an aminonitrophenol, a diaminonitrobenzene, or an aminonitrobenzenethiol, more preferably 2-amino-4-nitrophenol, 2-amino-5-nitrophenol, 3,4-diaminonitrobenzene, 2-amino-6-nitrophenol, 2-amino-4-nitrobenzenethiol, 2-amino-5-nitrobenzenethiol, or 2-amino-6-nitrobenzenethiol. The most preferred aminonitroarylex is 2-amino-4-nitrophenol.

The condensable nitroarylcarbonyl compound (II) and the aminonitroarylex (I) are condensed together, preferably at approximately equimolar concentrations and in the presence of a solvent that does not interfere with the condensation reaction. Preferred solvents are polar aprotic solvents such as dioxane and glycol ethers. More preferred solvents are ethylene glycol diethyl ether, diethylene glycol diethyl ether, diethylene glycol dimethyl ether, triethylene glycol dimethyl ether, and tetraethylene glycol dimethyl ether. The most preferred solvent is diethylene glycol dimethyl ether. The reaction is advantageously carried out at a sufficiently high temperature to promote the conversion at a desirable rate, preferably from about 50° C., more preferably from about 80° C., and most preferably from about 100° C., to about 250° C., more preferably to about 200° C., and most preferably to about 150° C. The reaction is most preferably carried out using diethylene glycol dimethyl ether.

The dinitroanilide (III) can be reduced then cyclized, or cyclized then reduced, to form the desired aminoarylaminoarazole. Although the step to form a nitroarylnitroarazole from the corresponding dinitroanilide (or alternatively, an aminoarylaminoarazole from the corresponding diaminoanilide) may be considered to be a condensation reaction, for the purposes of this description, this step is referred to as a cyclization step to distinguish it from the condensation reaction to form the dinitroanilide (III).

The following description addresses both the reduction of the dinitroanilide (III) to the corresponding diaminoanilide and the reduction of the nitroarylnitroarazole to the corresponding aminoarylaminoarazole.

Reduction is carried out by any suitable method that selectively reduces the nitro groups on either the dinitroanilide or the nitroarylnitroarazole. One such method is to contact the dinitroanilide or the nitroarylnitroarazole with hydrogen in the presence of a metal catalyst. Suitable metal catalysts include platinum, cobalt, nickel, titanium, zirconium, and hafnium. The catalyst is preferably supported on a porous support. Platinum and palladium are preferred catalysts, with platinum on carbon and palladium on carbon being particularly preferred. The amount of catalyst is chosen to provide an acceptable reaction rate, and is typically from about 1 part by weight of catalyst per 5 parts of the dinitroanilide to about 1 part by weight of catalyst per 5000 parts of the dinitroanilide.

In the preferred hydrogenation method, the dinitroanilide or the nitroarylnitroarazole is contacted with hydrogen at a partial pressure of up to about 5000 psig (35,000 kPa), preferably from about 25 psig to about 100 psig (170 to 690 kPa), and at a temperature at which a desired rate of reaction is achieved, preferably from about 25° C. to about 100° C. The reaction may be carried out in the presence of a solvent, preferably a polar solvent such as dioxane, methoxyethanol, or ethoxyethanol.

In the case where reduction to the diaminoanilide is performed before cyclization, cyclization to the corresponding aminoarylaminoarazole is generally carried out at a sufficient temperature and pressure to promote cyclization, yet minimize the formation of undesirable by-products. Preferably, the diaminoanilide is heated in the presence of a solvent such as dioxane or a glycol ether at a temperature from about 100° C. to about 300° C. The pressure at which the reaction is carried out is solvent dependent, but is generally in the range of 100 to 600 psi (700 to 4200 kPa).

In the case where cyclization of the dinitroanilide to the nitroarylnitroarazole is carried out prior to the reduction step, which is the preferred sequence of the process of the present invention, the condensation and cyclization steps can be conveniently carried out in a single reaction vessel (that is, a one-pot reaction). When the reaction to form the dinitroanilide is satisfactorily complete, as determined, for example, by analyzing an aliquot of the mixture by liquid chromatography, a sufficient amount of a suitable acid is added to the reaction mixture, and the mixture is heated to a sufficiently high temperature, to promote the cyclization reaction. Preferred acids include phosphoric acid, PPA, and $P_2O_5$, with PPA being especially preferred. One of the notable advantages of the process of the present invention is that the acid, preferably PPA, need not be used as the solvent, but rather as a reagent at substantially lower concentrations than prior art processes, thereby reducing waste streams, and providing an easier workup.

The volume to weight ratio of solvent to PPA is preferably not less than about 2:1, more preferably not less than about 3:1, and most preferably not less than about 5:1; and preferably not greater than about 100:1, more preferably not greater than about 40:1, and most preferably not greater than about 20:1. The temperature at which the cyclization reaction is carried out is preferably not less than about 100° C., more preferably not less than about 120° C., and most preferably not less than about 150° C.; and preferably not greater than about 280° C., more preferably not greater than about 230° C., and most preferably not greater than about 180° C. The reaction is most preferably carried out using refluxing diethylene glycol dimethyl ether.

The acid is preferably added to the reaction mixture containing the solvent and the dinitroanilide at a controlled rate to maintain a desired temperature. After the addition of the acid to the reaction mixture is complete, heating is continued until the desired amount of the nitroarylnitroarazole is formed. The nitroarylnitroarazole can be isolated by any suitable means, preferably by adding a sufficient amount of water to a hot solution of the nitroarylnitroarazole to precipitate the nitroarylarazole out of the solution when the solution is allowed to cool. More preferably, water is added to the solution maintained at about 100° C., followed by controlled cooling to precipitate the nitroarylnitroarazole out of the solution. The precipitate can then be isolated by filtration, for example, and purified by any suitable means, preferably by washing with water and an alcohol such as methanol or ethanol.

The reduction of the nitroarylnitroarazole to the aminoarylaminoarazole is advantageously carried out in the presence of a solvent, preferably a polar aprotic solvent such as dioxane or an alkoxyalcohol such as methoxyethanol, ethoxyethanol, 1-methoxy-2-propanol, and butoxyethanol. After satisfactory completion of the reaction, the catalyst is preferably removed by filtration at a temperature sufficiently high to prevent crystallization of the product. Precipitation of the final product can be promoted by the addition of water, particularly when an alkoxyethanol is used as a solvent. The water is preferably added at elevated temperatures, more preferably at about 60° C. to about 100° C. to form a slurry, which is then preferably heated under reflux for about 15 minutes to about 1 hour. The product is preferably cooled to ambient temperature, then filtered and washed, preferably with methanol or ethanol, then dried.

The aminoarylaminoarazole can be used to make PIBX polymers by reaction with an aromatic dianhydride, as described in the pending U.S. application of Hwang et al., entitled "Polyamic Acids and Methods to Convert Polyamic Acids into Polyimidebenzoxazole Films," Ser. No. 331,775, filed Oct. 31, 1994. This reaction is typically conducted in two stages. In the first stage, the 2-aminoarylaminoarazole and the dianhydride are reacted to form a polyamic acid. This is readily accomplished by contacting the dianhydride and the aminoarylarazole at a temperature of from about −20° C. to about 100° C. in a polar solvent. The resulting polyamic acid may then be convened to the PIBX by condensing some or all of the amic acid linkages. This condensation is conveniently accomplished by heating the polyamic acid to an elevated temperature up to about 600° C., but which is preferably about 160° C. to about 280° C. Alternatively, a ring-closure agent such as acetic anhydride or salts thereof may be contacted with the polyamic acid to promote formation of imide rings. Following the imidization reaction, it is preferred to further heat the PIBX to a temperature from about 300° C. to about 600° C., which improves tensile properties of the polymer.

The PIBX polymer can be used to make films, fibers, or other shaped articles. Such articles are conveniently prepared by forming a solution of the PIBX in a suitable solvent and extruding, coating, casting, or spraying the solution. Preferably, however, such articles are prepared from the polyamic acid solution, which is imidized after the shaped article is formed.

The following examples are for illustrative purposes only and are not intended to limit the scope of this invention.

EXAMPLE 1

Preparation of 2-(4-aminophenyl)-5-aminobenzoxazole Reduction Followed by Cyclization Step A: Preparation of 4,4'-dinitro-2-hydroxybenzanilide 4-Nitrobenzoyl chloride (58 g, 0.31 mol) dissolved in 250 mL of dioxane was combined with 2-amino-4-nitrophenol (46.2 g, 0.30 mol) dissolved in 1250 mL of dioxane in a 3-necked, 3-liter round bottom flask equipped with a condenser, a mechanical stirrer, and a heater. The solution was refluxed for 1 hour, then cooled and filtered to give 84.5 g (93.4 percent yield) of 4,4'-dinitro-2-hydroxybenzanilide.

Step B: Preparation of 4,4'-diamino-2-hydroxybenzanilide 4,4'-Dinitro-2-hydroxybenzanilide (20.0 g, 0.066 mol), dioxane (300 mL), and 10 percent Pd/C were placed in a 600 mL Hastelloy C Parr Reactor. The material was hydrogenated at 100° C. and 150 psi (1033 kPa) of hydrogen for 16 hours, after which the reactor was allowed to cool and hydrogen was vented off. The catalyst was filtered and the major portion of the solution was set aside for Step C, while dioxane was removed in vacuo from a small portion of the solution to give a product having a melting point of 235° C. to 238° C.

Step C: Preparation of 2-(4-aminophenyl)-5-aminobenzoxazole

The solution containing 4,4'-diamino-2-hydroxybenzanilide and dioxane from Step B was heated in the Parr Reactor at 250° C. for 24 hours, after which the solvent was removed and the product recrystallized for ethoxyethanol. The melting point was found to be 226° C. to 228° C., and IR, NMR, and GC-MS spectroscopy confirmed the product was 2-(4-aminophenyl)-5-aminobenzoxazole.

EXAMPLE 2

Preparation of 2-(4-aminophenyl)-5-aminobenzoxazole Cyclization Followed by Reduction Step A: Preparation of 2-(4-nitrophenyl)-5-nitrobenzoxazole 2-Amino-4-nitrophenol (46.2 g, 0.3 mol) was dissolved in diglyme (1250 mL) and added to a 3-necked, 3-liter flask equipped with a condenser, a mechanical stirrer, and a heater. 4-Nitrobenzoyl chloride (57 g, 0.3 mol) was dissolved in diglyme (250 mL) and added to the flask. The mixture was heated, with stirring, to 120° C. for 1 hour, whereupon polyphosphoric acid (90 g) was added. Heating was continued at 150° C. to 160° C. for an additional 1 hour. The reaction mixture was cooled to 110° C. to 120° C. and deionized water (500 mL) was added over a period of 15 to 30 minutes while the mixture was maintained at 100° C. The reaction mixture was cooled, and the precipitated product was filtered and washed with methanol (300 mL), then dried. The melting point was found to be 253° C. to 255° C. The overall yield was 95 percent with an assay of 100 percent by liquid chromatography.

Step B: Preparation of 2-(-4-aminophenyl)-5-aminobenzoxazole 2-(4-Nitrophenyl)-5-nitrobenzoxazole (30 g, 0.105 mol), ethoxyethanol (300 mL) and 10 percent Pd/C (300 mg) were placed in a 600 mL Parr Reactor. The reactor was heated to 70° C. at 50 psi hydrogen (340 kPa) for 3 hours, then 90° C. at 150 psi hydrogen (1033 kPa) for an additional 16 hours. After the hydrogen was vented off, the solution was filtered hot under nitrogen. A portion of the solvent (100 mL) was removed from the solution and deionized water (100 mL) was added thereto, causing product to precipitate. The solution containing the precipitated product was stirred and refluxed for 1 hour. The solution was cooled to room temperature, and the product was filtered and washed with methanol (50 mL). The product was dried and 20.7 g (87 percent yield) of an off-white solid having a melting point of 226° C. to 228° C. was obtained.

What is claimed is:

1. A process of preparing an aminoarylaminoarazole having the formula:

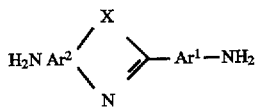

comprising the steps of:

a) condensing a condensable nitroarylcarbonyl compound having the formula;

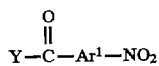

with a compound having the formula:

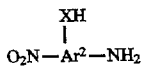

to form an anilide having the formula:

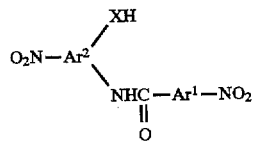

wherein $Ar^1$ and $Ar^2$ are each aromatic groups; X is S, NH or O; Y is Cl, Br, $OC_{1-4}$alkyl, or O-phenyl; and the —XH and —NHC(O)$Ar^1NO_2$ groups are connected to adjacent carbon atoms on $Ar^2$; and b) cyclizing and reducing the anilide under such conditions to form the aminoarylaminoarazole.

2. The process of claim 1 wherein the condensable nitroarylcarbonyl compound is a nitrobenzoyl halide, and the anilide in (a) is prepared at a temperature from about 100° C. to about 280° C. in a polar aprotic solvent selected from the group consisting of dioxane, ethylene glycol diethyl ether, diethylene glycol diethyl ether, diethylene glycol dimethyl ether, triethylene glycol dimethyl ether, and tetraethylene glycol dimethyl ether.

3. The process of claim 2 wherein the anilide is cyclized then reduced by the steps of a) adding a sufficient amount of a phosphorus-containing acid to a solution containing the anilide and the polar aprotic solvent to promote formation of a nitroarylnitroarazole having the formula:

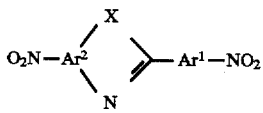

wherein Ar$^1$, Ar$^2$, and X, are as previously defined, then b) reducing the nitroarylnitroarazole to form the aminoarylaminoarazole.

4. The process of claim 3 wherein the volume to weight ratio of the polar aprotic solvent to the phosphorus-containing acid is from about 3:1 to about 20:1, and the phosphorus-containing acid is polyphosphoric acid.

5. The process of claim 4 wherein the nitroarylnitroarazole is reduced by hydrogen and a metal catalyst in the presence of an alkoxyalcohol solvent selected from the group consisting of methoxyethanol, ethoxyethanol, 1-methoxy-2-propanol, and butoxyethanol.

6. The process of claim 5 wherein the alkoxyalcohol solvent is ethoxyethanol.

7. The process of claim 6 wherein the polar aprotic solvent is diethylene glycol dimethyl ether.

8. The process of claim 7 wherein the aminoarylaminoarazole is 2-(4-aminophenyl)-5-aminobenzoxazole.

9. The process of claim 1 wherein the anilide is first reduced under such conditions to form a diaminoanilide and the diaminoanilide is heated sufficiently to form the aminoarylaminoarazole.

10. A process of preparing an aminophenylaminobenzazole represented by the following formula:

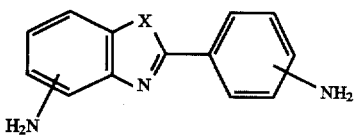

where X is S, NH, or O, comprising the steps of:

a) condensing a condensable nitrophenylcarbonyl compound with an aminonitrophenol, a diaminonitrobenzene, or an aminonitrobenzenethiol in the presence of a polar aprotic solvent selected from the group consisting of dioxane, ethylene glycol diethyl ether, diethylene glycol diethyl ether, diethylene glycol dimethyl ether, triethylene glycol dimethyl ether, and tetraethylene glycol dimethyl ether, and at a temperature from about 100° C. to about 280° C., to form a dinitrobenzanilide having the formula:

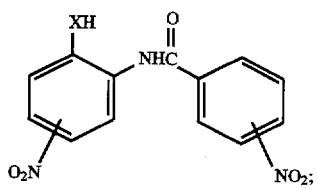

b) adding a sufficient amount of polyphosphoric acid and heat to a solution containing the polar aprotic solvent and the dinitrobenzanilide to promote the formation of a nitrophenylnitrobenzazole represented by the formula:

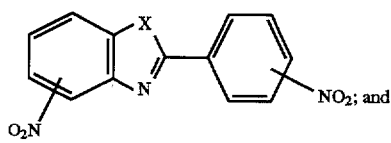

c) reducing the nitrophenylnitrobenzazole with hydrogen and a metal catalyst under such conditions to form the aminophenylaminobenzazole.

11. The process of claim 10 wherein the condensable nitroarylcarbonyl compound is nitrobenzoyl chloride and the aminonitrophenol is 2-amino-4nitrophenol.

12. The process of claim 10 wherein in step (b), the volume to weight ratio of the solvent to the polyphosphoric acid is from about 5:1 to about 10:1.

13. The process of claim 10 wherein the reduction step (c) is carried out in a alkoxyalcohol solvent selected from the group consisting of methoxyethanol, ethoxyethanol, 1-methoxy-2-propanol, and butoxyethanol.

14. The process of claim 13 wherein the nitrobenzoyl halide is nitrobenzoyl chloride and the aminonitrophenol is 2-amino-4-nitrophenol.

15. A process of preparing an aminoarylaminoarazole having the formula:

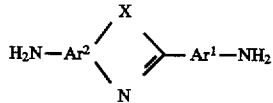

comprising the step of condensing a condensable nitroarylcarbonyl compound having the formula:

with a compound having the formula:

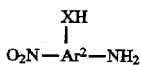

in the presence of a polar aprotic solvent selected from the group consisting of dioxane, ethylene glycol diethyl ether, diethylene glycol diethyl ether, diethylene glycol dimethyl ether, triethylene glycol dimethyl ether, and tetraethylene glycol dimethyl ether, and at a temperature of from about 100° C. to about 280° C., to form an anilide having the formula:

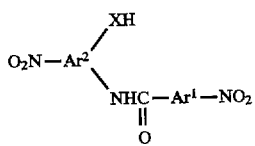

wherein $Ar^1$ and $Ar^2$ are each aromatic groups; X is S, NH, or O; Y is Cl, Br, $OC_{1-4}$alkyl, OH, or O-phenyl; and the —XH and —NHC(O)$Ar^1NO_2$ groups are connected to adjacent carbon atoms on $Ar^2$.

16. The process of claim 15 wherein the anilide is prepared by condensing 2-amino-4-nitrophenol with nitrobenzoyl chloride.

17. The process of claim 16 wherein a solution containing the anilide and the polar aprotic solvent is contacted with polyphosphoric acid and heated to a temperature from about 100° C. to about 280° C. to form 2-(4-nitrophenyl)-5-nitrobenzoxazole.

18. The process of claim 17 wherein the 2-(4-nitrophenyl)-5-nitrobenzoxazole is reduced by hydrogen and palladium or platinum over carbon in the presence of ethoxyethanol under such conditions to form 2-(4-aminophenyl)-5-aminobenzoxazole.

* * * * *